United States Patent
Bringhen et al.

[11] Patent Number: 6,165,451
[45] Date of Patent: Dec. 26, 2000

[54] COSMETIC LIGHT SCREENING COMPOSITION

[75] Inventors: Alain Bringhen, Choulex; Hans Ulrich Gonzenbach, Geneva; Rolf Schwarzenbach, Winterthur, all of Switzerland; Dominique Sidrac, Saint-Julien, France

[73] Assignee: Roche Vitamins Inc., Parsippany, N.J.

[21] Appl. No.: 09/494,804

[22] Filed: Jan. 31, 2000

[30] Foreign Application Priority Data

Feb. 8, 1999 [EP] European Pat. Off. ............ 99102456

[51] Int. Cl.⁷ .................... A61K 7/42; A61K 7/44; A61K 7/00
[52] U.S. Cl. ................ 424/59; 424/60; 424/400; 424/401
[58] Field of Search ................ 424/59, 60, 400, 424/401

[56] References Cited

FOREIGN PATENT DOCUMENTS

| | | |
|---|---|---|
| 2244556 | 2/1999 | Canada . |
| 0 895 776 | 2/1999 | European Pat. Off. . |
| 0 895 776 A2 | 2/1999 | European Pat. Off. . |

*Primary Examiner*—Shelley A. Dodson
*Attorney, Agent, or Firm*—Mark E. Waddell; Stephen M. Haracz; Bryan Cave LLP

[57] ABSTRACT

The invention relates to cosmetic light screening compositions containing a) a compound of formula I

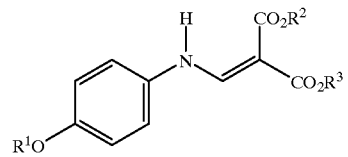

wherein
$R^1$ is a $C_{1-8}$ straight or branched alkyl chain, and
$R^2$ and $R^3$ are each independently a $C_{1-8}$ straight or branched alkyl chain;

b) common UV-B and/or common UV-A screening agents; and c) a cosmetically acceptable carrier.

23 Claims, No Drawings

COSMETIC LIGHT SCREENING COMPOSITION

FIELD OF THE INVENTION

The invention relates to cosmetic light screening compositions for protecting skin and/or hair against ultraviolet radiation. Such compositions contain new synergistic mixtures of light screening compounds. In particular, the invention relates to cosmetic light screening compositions containing an anilinomethylene propanedioic acid ester in combination with common UV-B and/or UV-A screening agents.

SUMMARY OF THE INVENTION

One embodiment of the present invention is a sunscreen composition that includes a compound of formula I:

[Structure I]

wherein $R^1$ is a $C_{1-8}$ straight or branched alkyl chain, and $R^2$ and $R^3$ are each independently a $C_{1-8}$ straight or branched alkyl chain; a UV screening agent selected from the group consisting of UV-B screening agents, UV-A screening agents, and mixtures thereof; and a cosmetically acceptable carrier.

In this embodiment, the UV-B screening agent may be, for example, an organosiloxane of formula II:

[Structure II]

wherein

R is methyl;

A is a compound of formula IIa or IIb:

[Structure IIa]

[Structure IIb]

r has a statistical mean value of about 4; and
s has a statistical mean value of about 60.

In this embodiment, the UV-A screening agent may be, for example, 4-tert. butyl-4'-methoxydibenzoyl-methane optionally stabilized by octocrylene, methylbenzylidene camphor, or a compound of formula II.

In another embodiment of the present invention, a method of treating human skin or hair with a sunscreen composition is provided. This method includes administering to the hair or skin of a human an effective amount of a composition a, defined above, wherein the UV screening agent is an UV-B screening agent.

A method of treating human skin or hair with a sunscreen composition is also provided. This method includes administering to the hair or skin of a human an effective amount a composition as defined above, wherein the UV screening agent is an UV-A screening agent.

DETAILED DESCRIPTION OF THE INVENTION

In the present invention, the sunscreen compositions contain, in a cosmetically acceptable carrier, a) a compound of formula I

[Structure I]

wherein $R^1$ is a $C_{1-8}$ straight or branched alkyl chain, and $R^2$ and $R^3$ are each independently a $C_{1-8}$ straight or branched alkyl chain; and b) common UV-B and/or UV-A screening agents. The combination of the compound of formula I and UV-B and/or UV-A screening agents provides synergistically enhanced protection indices as set forth in more detail below.

As used herein, the term "$C_{1-8}$ straight or branched alkyl chain" refers to groups such as for example, methyl, ethyl, n-propyl, isopropyl, n-butyl, tert. butyl, pentyl, heptyl, 2-ethylhexyl and the like. A preferred branched $C_{1-8}$ alkyl chain is 2-ethylhexyl.

Preferably $R^2$ and $R^3$ are each independently a straight $C_{1-4}$ alkyl chain, e.g. methyl, ethyl or n-butyl, such as for example, $R^2$ and $R^3$ are ethyl.

$R^1$ is preferably a straight $C_{1-4}$ alkyl chain, e.g. methyl, ethyl or n-butyl, more preferably ethyl.

The compounds of formula I and their manufacture are described in the European Patent Publication EP 0895776 A2, which is incorporated by reference as if recited in full herein.

Compounds of formula I have their absorption maxima between the classical UV-B and UV-A screening agents and especially and surprisingly increase the protective effect of common UV-B and/or UV-A screening agents, although the absorption maxima of compounds of formula I do not lie in this region, but in the region of about 320 to about 340 nm.

As used herein, the term "common UV-B screening agents", is intended to mean those agents whose absorption maxima is between about 290 and about 320 nm. The following list sets forth examples of common UV-B screening agents that may be used. in the present invention.

Acrylates such as 2-ethylhexyl 2-cyano-3,3-diphenylacrylate (octocrylene, PARSOL 340), ethyl 2-cyano-3,3-diphenylacrylate and the like;

Camphor derivatives such as 4-methyl benzylidene camphor (PARSOL 5000), 3-benzylidene camphor, camphor benzalkonium methosulfate, polyacrylamidomethyl benzylidene camphor, sulfo benzylidene camphor, sulphomethyl benzylidene camphor, therephthalidene dicamphor sulfonic acid and the like;

Cinnamate derivatives such as octyl methoxycinnamate (PARSOL MCX), ethoxyethyl methoxycinnamate, diethanolamine methoxycinnamate (PARSOL Hydro), isoamyl methoxycinnamate, and the like, as well as cinnamic acid derivatives bonded to siloxanes;

Organosiloxane compounds containing benzmalonate groups as described in EP 0358584 B1, EP 0538431 B1 and EP 0709080 A1;

Pigments such as microparticulated $TiO_2$, and the like.

As used herein, the term "microparticulated" is intended to mean a particle size from about 5 nm to about 200 nm, particularly from about 15 nm to about 100 nm. The $TiO_2$ particles may also be coated with metal oxides such as, for example, aluminum or zirconium oxides or with organic coatings such as, for example, polyols, methicone, aluminum stearate, and alkyl silane.

Imidazole derivatives such as for example, 2-phenyl benzimidazole sulfonic acid and its salts (PARSOL HS). Salts of 2-phenyl benzimidazole sulfonic acid are e.g. alkali salts such as sodium- or potassium salts, ammonium salts, morpholine salts, salts of primary, sec. and tert. amines like monoethanolamine salts, diethanolamine salts and the like.

Salicylate derivatives such as isopropylbenzyl salicylate, benzyl salicylate, butyl salicylate, octyl salicylate (NEO HELIOPAN OS), isooctyl salicylate or homomenthyl salicylate (homosalate, HELIOPAN) and the like;

Triazone derivatives such as octyl triazone (UVINUL T-150), dioctyl butamido triazone (UVASORB HEB) and the like.

As used herein, the term "common UV-A screening agents" is intended to mean agents whose absorption maxima is between about 320 and about 400 nm. The following list sets forth non-limiting examples of common UV-A screening agents that may be used in the present invention.

Dibenzoylmethane derivatives such as 4-tert. butyl-4'-methoxydibenzoylmethane (PARSOL 1789), dimethoxydibenzoylmethane, isopropyldibenzoylmethane and the like;

Benzotriazole derivatives such as 2,2'-methylene-bis-(6-(2H-benzotriazole-2-yl)-4-(1,1,3,3,-tetramethylbutyl)-phenol (TINOSORB M) and the like;

Pigments such as microparticulated ZnO and the like as defined above.

Because dibenzoylmethane derivatives are photolabile, it is necessary to photostabilize these UV-A screening agents. Thus, the term "common UV-A screening agent" also refers to dibenzoylmethane derivatives such as for example, PARSOL 1789 stabilized by the following stabilizing agents:

3,3-Diphenylacrylate derivatives as described in the European Patent Publications EP 0514491 B1 and EP 0780119 A1;

Benzyliden camphor derivatives as described in Deflandre, et al., U.S. Pat. No. 5 605 680;

Organosiloxanes containing benzmalonate groups as described in the European Patent Publications EP 0358584 B1, EP 0538431 B1 and EP 0709080 A1.

With regard to light screening compositions containing a compound of formula I and a common UV-B screening agent, the following compositions are preferred:

a) a sunscreen composition containing, in a cosmetically acceptable carrier, a compound of formula I wherein $R^1$, $R^2$ and $R^3$ are ethyl and octyl methoxycinnamate (PARSOL MCX);

b) a sunscreen composition containing in a cosmetically acceptable carrier a compound of formula I wherein $R^1$, $R^2$ and $R^3$ are ethyl and the following polysiloxane compound of formula II (described in the European Patent Publication EP 0709080 A1) and hereinafter referred to as "Polysiloxane A:"

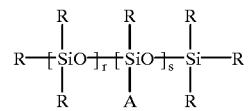

wherein
R is methyl; and
A is a compound according to formula IIa or IIb;

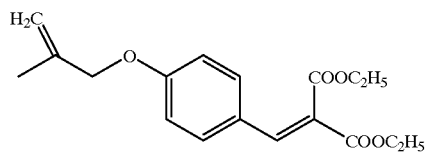

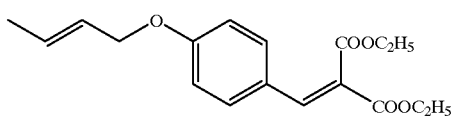

r has a statistical mean value of about 4; and
s has a statistical mean value of about 60.

c) a sunscreen composition containing, in a cosmetically acceptable carrier, a compound of formula I wherein $R^1$, $R^2$ and $R^3$ are ethyl and microparticulated $TiO_2$;

d) a sunscreen composition containing, in a cosmetically acceptable carrier, a compound of formula I wherein $R^1$, $R^2$ and $R^3$ are ethyl and 4-methyl benzylidene camphor (PARSOL 5000);

e) a sunscreen composition containing a compound of formula I wherein $R^1$, $R^2$ and $R^3$ are ethyl and 2-ethylhexyl 2-cyano-3,3-diphenylacrylate (octocrylene, PARSOL 340).

With regard to light screening compositions containing a compound of formula I and a common UV-A screening agent, the following compositions are preferred:

a) a sunscreen composition containing a compound of formula I wherein $R^1$, $R^2$ and $R^3$ are ethyl and 4-tert. butyl-4'-methoxydibenzoyl-methane (PARSOL 1789), optionally stabilized by octocrylene (PARSOL 340), methylbenzylidene camphor (PARSOL 5000) or "Polysiloxane A";

b) a sunscreen composition containing a compound of formula I wherein $R^1$, $R^2$ and $R^3$ are ethyl and 2,2'-methylene-bis-(6-(2H-benzotriazole-2-yl)-4-(1,1,3,3,-tetramethylbutyl)-phenol (TINOSORB M);

c) a sunscreen composition containing a compound of formula I wherein $R^1$, $R^2$ and $R^3$ are ethyl and microparticulated ZnO.

The preparation of light screening compositions, especially of preparations for skin protection and, respectively, sunscreen preparations for everyday cosmetics is well known to the skilled artisan in this field. For example, such a preparation may include incorporating a compound of formula I and common UV-B and/or UV-A screening agents optionally together with stabilizers as described above in a typical cosmetic base used for light screening agents.

In the preparation of the light screening compositions of the present invention, the amount of the formula I compounds and common UV-B and/or UV-A screening agents is not critical. Suitable amounts of each compound used in the compositions of the present invention are set forth below:

Compound of formula I: about 0.5 wt % to about 10 wt %,

Polysiloxane A: about 0.5 to about 15 wt %,

PARSOL MCX: about 0.5 to about 10 wt %,

PARSOL 340: about 0.5 to about 10 wt %,

PARSOL 1789: about 0.5 to about 5 wt %,

PARSOL 5000: about 0.5 to about 4 wt %,

TINOSORB M: about 0.5 to about 10 wt %, $TiO_2$: about 0.5 to about 25 wt %,

ZnO: about 0.5 to about 20 wt %.

Where convenient, the light screening compositions of the present invention may also be combined with other conventional UV-A, and respectively, UV-B screening agents during this incorporation.

Thus, light screening compositions containing a compound of formula I and a common UV-B screening agent may be further combined with other common UV-A screening agents such as PARSOL 1789, ZnO, TINOSORB M and the like.

Furthermore, a light screening composition containing a compound of formula I and a common UV-A screening agent may be further combined with other common UV-B screening agent, such as PARSOL MCX, $TiO_2$, Polysiloxane A and the like.

The following examples are provided to further illustrate methods of preparation of the compositions of the present invention, as well as certain physical properties and uses thereof. These examples are illustrative only and are not intended to limit the scope of the invention in any way.

In these examples, the abbreviations and trade names selected have the following significance:

| | |
|---|---|
| ARLACEL 481 | Glycerol sorbitan fatty acid ester sold by ICI |
| ARLACEL P135 | PEG-30 dipolyhydroxystearate sold by ICI |
| ARLAMOL E | POP-(15)-stearyl alcohol sold by ICI |
| ARLAMOL HD | Heptamethylnonane sold by ICI |
| BHT | Butylhydroxytoluol (2,6 di-tert butyl-4-methyl phenol) |
| BRIJ 72 | POE-(2)-stearyl alcohol sold by ICI |
| BRIJ 721 | POE-(21)-stearyl alcohol sold by ICI |
| CETIOL LC | Coco caprilate/caprate sold by Henkel |
| Cetyl alcohol | Cetyl alcohol sold by Henkel |
| CUTINA HR | Hydrogenated Castor oil sold by Henkel |
| EDETA BD | Disodium EDTA sold by BASF |
| ELFACOS C26 | Hydroxyoctacosanyl hydroxystearate sold by Akzo Nobel |
| FINSOL TN | C12–15 alkyl benzoate sold by Finetex Inc. |
| KELTROL | Xanthan gum sold by Kelco |
| KOH | Potassium hydroxide sold by Merck |
| LANETTE O | Cetearyl alcohol sold by Henkel |
| NIPAGIN M | Methylparabene sold by Henkel sold by Nipa Ltd. |
| PARSOL 340 | Octocrylene sold by Roche |
| PARSOL 1789 | Butyl Methoxydibenzoylmethane sold by Roche |
| PARSOL 5000 | 4-Methyl Benzylidene Camphor sold by Roche |
| PARSOL HS | 2-Phenyl benzimidazole sulfonic acid |
| PARSOL MCX | Octyl Methoxycinnamate sold by Roche |
| PBG 2 Stearate | Diethylene glycol monostearate sold by Croda |
| PEMULEN TR-1 | Acrylate/C10-30 alkyl acrylate crosspolymer sold by Goodrich |
| Petroleum Jelly | Petrolatum sold by Witco Corp. |
| PHENONIP | mixture of 4-hydroxybenzoic acid esters sold by Nipa |
| Propylene glycol | 1,2 propanediol sold by BASF |
| RICINOL | Castor oil sold by Givaudan-Roure |

-continued

| | |
|---|---|
| SATOL | Oleyi alcohol sold by Givaudan-Roure |
| SILBIONE oil 70047 V20 | Cyclomethicone sold by Rhône Poulenc |
| SILICONE 1401 | Cyclomethicone and dimethiconol sold by Dow Corning |
| SILICONE 200/100 cs | Dimethicone sold by Dow Corning |

EXAMPLE 1

Preparation of 2-(4-Ethoxy-anilinomethylene)-propanedioic acid diethyl ester

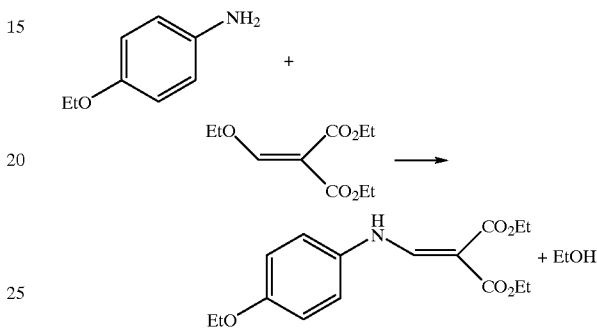

To 41.15 g (0.3 Mol) of p-phenetidine in 90 ml of hexane, 64.9 g (0.3 Mol) of diethyl ethoxymethylenemalonate was added dropwise with stirring at room temperature. After an additional hour of stirring at room temperature, the reaction mixture was cooled with an ice bath and the product crystallized spontaneously. The crude solid material was isolated by filtration and washed with hexane to give 78.3 g of the title product; white solid melting at 55–56° C. UV 329 nm (E=802).

EXAMPLE 2

Preparation of a sunscreen O/W lotion containing 5% of UV-filter as described in Examples 3 to 8

| Ingredients | % w/w |
|---|---|
| ARLAMOL E | 5.00 |
| ARLAMOL HD | 5.00 |
| BRIJ 72 | 3.00 |
| BRIJ 721 | 2.00 |
| UV-filter | 5.00 |
| ARLACEL P135 | 0.50 |
| LANETTE O | 5.00 |
| Stearic Acid | 1.50 |
| SILBIONE Oil 70047V20 | 1.00 |
| BHT | 0.10 |
| PHENONIP | 0.60 |
| Deionized Water | qsp to 100.00 |
| Xanthan Gum 1% solution | 6.00 |
| Propylene Glycol | 4.00 |
| UMORDAN P | 1.00 |

The organic phase containing the UV-filters was heated to 75° C., then the preheated aqueous phase (75° C.) was added while stirring. The resulting emulsion was cooled to ambient temperature.

The following Examples 3 to 5 refer to sunscreen compositions according to the present invention containing a compound of formula I and a common UV-B screening agent.

EXAMPLE 3

Three sunscreen formulations were prepared according to Example 2 with the following UV-screening agents were prepared:

Formulation No. 3/1: the UV-filter is the compound of Example 1 (2-(4-Ethoxy anilinomethylene)-propanedioic acid diethyl ester) at 5% w/w.

Formulation No. 3/2: the UV-filter is PARSOL MCX (Octyl Methoxycinnamate) at 5% w/w.

Formulation No. 3/3: the UV-filter is a mixture of 2.5% w/w of the compound of Example 1 and 2.5% w/w of PARSOL MCX.

Determination of the sun protection factor:

For each formulation, the sun protecting factor (SPF) was determined according to the method described by B. Diffey and J. Robson in J. Soc. Cosmet. Chem. 40, 127–133 (1989), which is hereby incorporated by reference as if recited in full herein.

The results are given in the following table:

| Sunscreen formulations | UV-filter | In vitro SPF | Expected SPF | Synergy |
|---|---|---|---|---|
| 3/1 | 5% compound of Ex. 1 | 15.2 | | |
| 3/2 | 5% PARSOL MCX | 11.3 | | |
| 3/3 | 2.5% compound of Ex. 1 + 2.5% PARSOL MCX | 19.8 | 13.3 | 49% |

In vitro SPF: Mean value of 5 determinations.
Expected SPF: Calculated by adding In vitro SPF-value of sunscreen Formulation Nos. 3/1 and 3/2, divided by 2 (2.5% of each instead of 5%).
Synergy: % deviation of In vitro SPF from expected (calculated) SPF.

Expected SPF: Calculated by adding In vitro SPF-value of sunscreen Formulation Nos. 3/1 and 3/2, divided by 2 (2.5% of each instead of 5%).

Synergy: % deviation of In vitro SPF from expected (calculated) SPF.

The combination of the compound of Example 1 and PARSOL MCX according to the invention shows an unproportional increase of the SPF. Usually, the SPF of filter combinations is very close to the calculated value from the performance of the single filters, therefore, there was a synergistic effect in this combination.

EXAMPLE 4

Three sunscreen formulations were prepared according to Example 2.

Formulation No. 4/1: the UV-filter is the compound of Example 1 (2-(4-Ethoxyanilinomethylene)-propanedioic acid diethyl ester) at 5% w/w.

Formulation No. 4/2: the UV-filter is $TiO_2$ at 5% w/w.

Formulation No. 4/3: the UV-filter is a mixture of 2.5 % w/w of the compound of Example 1 and 2.5 % w/w of $TiO_2$.

The results of the determination of the sun protection factor are given in the following table:

| Sunscreen formulations | UV-filter | In vitro SPF | Expected SPF | Synergy |
|---|---|---|---|---|
| 4/1 | 5% compound of Ex. 1 | 15.2 | | |
| 4/2 | 5% $TiO_2$ | 1.3 | | |
| 4/3 | 2.5% compound of Ex. 1 + 2.5% $TiO_2$ | 16.0 | 8.3 | 94% |

In vitro SPF: Mean value of 5 determinations.
Expected SPF: Calculated by adding In vitro SPF-value of sunscreen Formulation Nos. 4/1 and 4/2, divided by 2 (2.5% of each instead of 5%).
Synergy: % deviation of In vitro SPF from expected (calculated) SPF.

Expected SPF: Calculated by adding In vitro SPF-value of sunscreen Formulation Nos. 4/1 and 4/2, divided by 2 (2.5% of each instead of 5%).

Synergy: % deviation of In vitro SPF from expected (calculated) SPF.

The combination of the compound of Example 1 and $TiO_2$ according to the invention shows an unproportional increase of the SPF. Usually, the SPF of filter combinations is very close to the calculated value from the performance of the single filters, therefore, there was a synergistic effect in this combination.

EXAMPLE 5

Three sunscreen formulations were prepared according to Example 2.

Formulation No. 5/1: the UV-filter is the compound of Example 1 (2-(4-Ethoxy-anilinomethylene)-propanedioic acid diethyl ester) at 5% w/w.

Formulation No. 5/2: the UV-filter is Polysiloxane A at 5% w/w.

Formulation No. 5/3: the UV-filter is a mixture of 2.5% w/w of the compound of Example 1 and 2.5% w/w of Polysiloxane A.

The results of the determination of the sun protection factor are given in the following table:

| Sunscreen formulations | UV-filter | In vitro SPF | Expected SPF | Synergy |
|---|---|---|---|---|
| 5/1 | 5% compound of Ex. 1 | 15.2 | | |
| 5/2 | 5% Polysiloxane A | 3.4 | | |
| 5/3 | 2.5% compound of Ex. 1 + 2.5% Polysiloxane A | 12.3 | 9.3 | 32% |

In vitro SPF: Mean value of 5 determinations.
Expected SPF: Calculated by adding In vitro SPF-value of sunscreen Formulation Nos. 5/1 and 5/2, divided by 2 (2.5% of each instead of 5%).
Synergy: % deviation of In vitro SPF from expected (calculated) SPF.

Expected SPF: Calculated by adding In vitro SPF-value of sunscreen Formulation Nos. 5/1 and 5/2, divided by 2 (2.5% of each instead of 5%).

Synergy: % deviation of In vitro SPF from expected (calculated) SPF.

The combination of the compound from Example 1 and Polysiloxane A shows an unproportional increase of the SPF. Usually, the SPF of filter combinations is very close to the calculated value from the performance of the single filters, therefore, there was a synergistic effect in this combination.

The following Examples 6 to 8 refer to sunscreen compositions according to the present invention containing a compound of formula I and a common UV-A screening agent. In Examples 7 and 8, PARSOL 1789 is stabilized.

EXAMPLE 6

Three sunscreen formulations were prepared according to Example 2.

Formulation No. 6/1: the UV-filter is the compound of Example 1 (2-(4-Ethoxy-anilinomethylene)-propanedioic acid diethyl ester) at 5% w/w.

Formulation No. 6/2: the UV-filter is PARSOL 1789 (Butyl Methoxydibenzoylmethane) at 2.5% w/w.

Formulation No. 6/3: the UV-filter is a mixture of 2.5 % w/w of the compound of Example 1 and 1.25% w/w of PARSOL 1789.

Determination of the Erythemal UV-APF:

For each formulation, Erythemal UV-APF was determined. Erythemal UV-APF is an indicator of the UV-A protection property of a sunscreen product, and is calculated from $MPF_\lambda$, $E_\lambda$, $B_\lambda$, wherein $MPF_\lambda$, =Monochromatic protection factor, $E_\lambda$=Spectral irradiance of terrestrial sunlight under defined conditions (mid day mid summer sunlight at 40° N, solar zenith angle 20°); and $B_\lambda$=Erythemal Effectiveness (CIE).

Erythemal UV-APF for each Formulation was determined according to the method described by B. Diffey and J. Robson in J. Soc. Cosmet Chem., 40, 127–133 (1989), which reference is incorporated by reference as if recited in full herein.

The results of the determination of the Erythemal UV-A protection factor are given in the following table:

| Sunscreen formulations | UV-filter | In vitro UV-APF | Expected UV-APF | Synergy |
|---|---|---|---|---|
| 6/1 | 5% compound of Ex. 1 | 11.1 | | |
| 6/2 | 2.5% PARSOL 1789 | 9.7 | | |
| 6/3 | 2.5% compound of Ex. 1 + 2.5% PARSOL 1789 | 24.0 | 10.4 | 131% |

In vitro UV-A PF: Mean value of 5 determinations.
Expected UV-A PF: Calculated by adding In vitro UV-APF-value of sunscreen Formulation Nos. 6/1 and 6/2, divided by 2.
Synergy: % deviation of In vitro UV-APF from expected (calculated) UV-A PF.

Expected UV-A PF: Calculated by adding In vitro UV-APF-value of sunscreen Formulation Nos. 6/1 and 6/2, divided by 2.

Synergy: % deviation of In vitro UV-APF from expected (calculated) UV-A PF.

The combination of the compound of Example 1 and PARSOL 1789 according to the invention shows an unproportional increase of the UV-APF. Usually, the UV-APF of filter combinations is very close to the calculated value from the performance of the single filters, therefore, there was a synergistic effect in this combination.

EXAMPLE 7

Three sunscreen formulations were prepared according to Example 2.

Formulation No. 7/1: the UV-filter is the compound of Example 1 (2-(4-Ethoxy-anilinomethylene)-propanedioic acid diethyl ester) at 5% w/w.

Formulation No. 7/2: the UV-filter is a mixture of 1.7% w/w of PARSOL 1789 and 1.7% w/w of PARSOL 340.

Formulation No. 7/3: the UV-filter is a mixture of 3% w/w of the compound of Example 1 and 1% w/w of PARSOL 1789 and 1% w/w of PARSOL 340.

The results of the determination of the sun protection factor and the Erythemal UV-A protection factor are set forth in the two following tables:

| Sunscreen formulations | UV-filter | In vitro SPF | Expected SPF | Synergy |
|---|---|---|---|---|
| 7/1 | 5% compound of Ex. 1 | 15.2 | | |
| 7/2 | 1.7% PARSOL 1789 + 1.7% PARSOL 340 | 3.4 | | |
| 7/3 | 3% compound of Ex. 1, 1.7% PARSOL 1789 + 1.7% PARSOL 340 | 13.0 | 10.9 | 19% |

In vitro SPF: Mean value of 5 determinations.
Expected SPF: Calculated by adding In vitro SPF-value of sunscreen Formulation 7/1 and 7/2, divided 1.7.
Synergy: % deviation of In vitro SPF from expected (calculated) SPF.

Expected SPF: Calculated by adding In vitro SPF-value of sunscreen Formulation 7/1 and 7/2, divided by 1.7.

Synergy:% deviation of In vitro SPF from expected (calculated) SPF.

| Sunscreen formulations | UV-filter | In vitro UV-APF | Expected UV-APF | Synergy |
|---|---|---|---|---|
| 7/1 | 5% compound of Ex. 1 | 11.1 | | |
| 7/2 | 1.7% PARSOL 1789 + 1.7% PARSOL 340 | 6.2 | | |
| 7/3 | 3% compound of Ex. 1, 1.7% PARSOL 1789 + 1.7% PARSOL 340 | 11.5 | 10.2 | 13% |

In vitro UV-APF: Mean value of 5 determinations.
Expected UV-APF: Calculated by adding In vitro UV-APF-value of sunscreen Formulation Nos. 7/1 and 7/2, divided by 1.7.
Synergy: % deviation of In vitro UV-APF from expected (calculated) UV-APF.

Expected UV-APF: Calculated by adding In vitro UV-APF-value of sunscreen ormulation Nos. 7/1 and 7/2, divided by 1.7.

Synergy: % deviation of In vitro UV-APF from expected (calculated) UV-APF.

The combination of the compound of Example 1 and a mixture of PARSOL 1789 and PARSOL 340 according to the invention show an unproportional increase of the SPF and of the UV-A PF as well. There was at the same time a synergistic effect of the UV-B and of the UV-A protection.

EXAMPLE 8

Three sunscreen formulations were prepared according to Example 2.

Formulation No. 8/1: the UV-filter is the compound of Example 1 (2-(4-Ethoxy-anilinomethylene)-propanedioic acid diethyl ester) at 5% w/w.

Formulation No. 8/2: the UV-filter is a mixture of 1.7% w/w of PARSOL 1789 and 1.7% w/w of PARSOL 5000.

Formulation No. 8/3: the UV-filter is a mixture of 3% w/w of the compound of Example 1 and 1% w/w of PARSOL 1789 and 1% w/w of PARSOL 5000.

The results of the determination of the sun protection factor and the Erythemal UV-A protection factor are given in the two following tables:

| Sunscreen formulations | UV-filter | In vitro SPF | Expected SPF | Synergy |
|---|---|---|---|---|
| 8/1 | 5% compound of Ex. 1 | 15.2 | | |
| 8/2 | 1.7% PARSOL 1789 + 1.7% PARSOL 5000 | 7.9 | | |
| 8/3 | 3% compound of Ex. 1, 1.7% PARSOL 1789 + 1.7% PARSOL 5000 | 17.2 | 13.6 | 27% |

In vitro SPF: Mean value of 5 determinations.
Expected SPF: Calculated by adding In vitro SPF-value of sunscreen Formulation 8/1 and 8/2, divided 1.7.
Synergy: % deviation of In vitro SPF from expected (calculated) SPF.

Expected SPF: Calculated by adding In vitro SPF-value of sunscreen Formulation Nos. 8/1 and 8/2, divided by 1.7.

Synergy: % deviation of In vitro SPF from expected (calculated) SPF.

| Sunscreen formulations | UV-filter | In vitro UV-APF | Expected UV-APF | Synergy |
|---|---|---|---|---|
| 8/1 | 5% compound of Ex. 1 | 11.1 | | |
| 8/2 | 1.7% PARSOL 1789 + 1.7% PARSOL 5000 | 6.4 | | |
| 8/3 | 3% compound of Ex. 1, 1.7% PARSOL 1789 + 1.7% PARSOL 5000 | 12.5 | 10.3 | 21% |

In vitro UV-APF: Mean value of 5 determinations.
Expected UV-A PF: Calculated by adding In vitro UV-A PF-value of sunscreen Formulation Nos. 8/1 and 8/2, divided by 1.7.
Synergy: % deviation of In vitro UV-APF from expected (calculated) UV-APF.

Expected UV-A PF: Calculated by adding In vitro UV-A PF -value of sunscreen Formulation Nos. 8/1 and 8/2, divided by 1.7.

Synergy: % deviation of In vitro UV-APF from expected (calculated) UV-APF.

The combination of the compound of Example 1 and a mixture of PARSOL 1789 and PARSOL 5000 according to the invention show an unproportional increase of the SPF and of the UV-A PF as well. There was at the same time a synergistic effect of the UV-B and of the UV-A protection Examples 9 to 12 refer to different sunscreen formulations according to the present invention.

EXAMPLE 9

A sunscreen oil-in-water lotion was prepared with the following ingredients:

| Part | Ingredients | % w/w |
|---|---|---|
| A) | BRIJ 72 | 3.00 |
| | BRIJ 721 | 2.00 |
| | PEG 2 Stearate | 0.25 |
| | Compound of Example 1 | 2.50 |
| | PARSOL MCX | 7.50 |
| | Cetyl Alcohol | 1.00 |
| | CETIOL LC | 7.00 |
| | EDETA BD | 0.10 |
| | PHENONIP | 0.60 |
| B) | Deionized Water | qsp 100 |
| | PEMULEN TR-1 (1% solution) | 20.00 |
| | Propylene Glycol | 5.00 |
| | NIPAGIN M | 0.15 |
| | KOH (10% solution) | qsp pH7 |

The organic phase A) containing the UV-filters was heated to 75° C., then the pre-heated aqueous phase B) (75° C.) was added while stirring. The resulting emulsion was cooled to ambient temperature. The pH value was corrected with KOH 10%.

EXAMPLE 10

A sunscreen water-in-SILICONE emulsion was prepared with the following ingredients:

| Part | Ingredients | % w/w |
|---|---|---|
| A) | SILICONE 1401 Substantivity Aid Fluid | 10.00 |
| | SILICONE 3225C Formulation Aid | 10.00 |
| B) | Compound of Example 1 | 5.00 |
| | $TiO_2$ | 5.00 |
| | ZnO | 2.00 |
| | FINSOLv TN | 5.00 |
| | EDETA BD | 0.10 |
| | PHENONIP | 0.60 |
| C) | Deionized Water | Qsp100 |
| | Propylene Glycol | 3.00 |
| | Sodium Chloride | 4.00 |

The ingredients of Part A were mixed at room temperature. When homogeneous, the ingredients of Part B were added to Part A and pre-heated to 85° C. while mixing. The ingredients of Part C were added to the mixture of Parts A and B and pre-heated to 75° C., slowly and gradually, while mixing with a mild turbine agitation, then a rapid turbine agitation The whole mixture was cooled to 40° C. The water loss was compensated and stirring was continued while cooling to ambient temperature. Then the preparation was passed three times through a homogenizer.

EXAMPLE 11

An oil-in-water emulsion was prepared with the following ingredients:

| Part | Ingredients | % w/w |
|---|---|---|
| A) | Compound of Example 1 | 5.00 |
|  | PARSOL 340 | 5.00 |
|  | PARSOL 1789 | 2.00 |
|  | ARLACEL 481 | 9.00 |
|  | ELFACOS C26 | 5.00 |
|  | Petroleum Jelly | 2.00 |
|  | Vaselin Oil | 10.00 |
|  | CETIOL LC | 10.00 |
|  | PHENONIP | 0.60 |
| B) | Deionized Water | qsp 100 |
|  | Sorbitol 70% | 5.00 |
|  | Glycerin | 3.00 |
|  | EDETA BD | 0.10 |

The organic phase A) containing the UV-filters was heated to 75° C., then the pre-heated aqueous phase B) (75° C.) was added to the organic phase A) while stirring. The resulting emulsion was cooled to ambient temperature.

EXAMPLE 12

A lipstick was prepared with the following ingredients

| Ingredients | % w/w |
|---|---|
| Compound of Example 1 | 2.00 |
| PARSOL MCX | 2.00 |
| Satol | 20.00 |
| Ricinol | 12.00 |
| CUTINA HR | 3.00 |
| Texwax MH 181 | 30.00 |
| Vaselin Oil | qsp 100 |
| Petroleum Jelly | 11.00 |
| SILICONE 200/100 cs | 3.50 |
| Propylene Glycol | 3.00 |
| Butylated Hydroxytoluene | 0.02 |
| EDETA BD | 0.02 |

The ingredients were heated to 85° C. while stirring, until complete dissolution was reached. When homogeneous, the hot preparation was poured into a mold.

The invention being thus described, it will be obvious that the same may be varied in many ways. Such variations are not to be regarded as a departure from the spirit and scope of the invention and all such modifications are intended to be included within the scope of the following claims.

What is claimed is:

1. A sunscreen composition comprising
   (a) a compound of formula I:

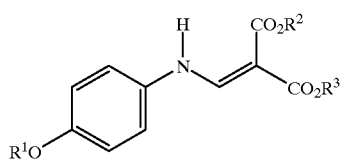

wherein
   $R^1$ is a $C_{1-8}$ straight or branched alkyl chain, and
   $R^2$ and $R^3$ are each independently a $C_{1-8}$ straight or branched alkyl chain;
   b) a UV screening agent selected from the group consisting of UV-B screening agents, UV-A screening agents, and mixtures thereof; and
   c) a cosmetically acceptable carrier.

2. A sunscreen composition according to claim 1 wherein $R^1$, $R^2$ and $R^3$ are each independently a straight $C_{1-4}$ alkyl chain.

3. A sunscreen composition according to claim 2 wherein $R^1$, $R^2$ and $R^3$ are each independently ethyl.

4. A sunscreen composition according to claim 1 wherein the UV screening agent is a UV-B screening agent.

5. A sunscreen composition according to claim 2 wherein the UV screening agent is a UV-B screening agent.

6. A sunscreen composition according to claim 4 wherein the UV-B screening agent is octylmethoxycinnamate.

7. A sunscreen composition according to claim 4 wherein the UV-B screening gent is an organosiloxane of formula II:

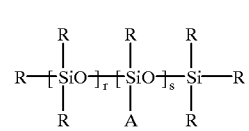

wherein
R is methyl;
A is a compound of formula IIa or IIb:

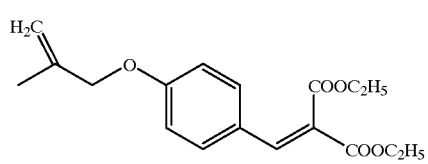

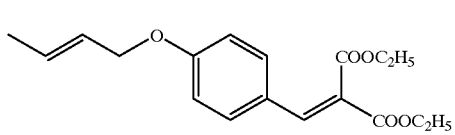

r has a statistical mean value of about 4;
s has a statistical mean value of about 60.

8. A sunscreen composition according to claim 4 wherein the UV-B screening agent is microparticulated $TiO_2$.

9. A sunscreen composition according to claim 4 wherein the UV-B screening agent is 4-methyl benzylidene camphor.

10. A sunscreen composition according to claim 4 wherein the UV-B screening agent is octocrylene.

11. A sunscreen composition according to claim 1 wherein the UV screening agent is a UV-A screening agent.

12. A sunscreen composition according to claim 2 wherein the screening agent is a UV-A screening agent.

13. A sunscreen composition according to claim 11 wherein the UV-A screening agent is 4-tert. butyl-4'-methoxydibenzoyl-methane optionally stabilized by octocrylene, methylbenzylidene camphor, or a compound of formula II.

14. A sunscreen composition according to claim 11 wherein the UV-A screening agent is 2,2'-methylene-bis-(6-(2H-benzotriazole-2-yl)-4-(1,1,3,3,-tetramethylbutyl)-phenol.

15. A sunscreen composition according to claim 11 wherein the UV-A screening agent is microparticulated ZnO.

16. A sunscreen composition according to claim 4 further comprising a UV-A screening agent.

17. A sunscreen composition according to claim 16 wherein the UV-A screening agent is selected from the group consisting of 4-tert. butyl-4'-methoxydibenzoyl-methane, 2,2'-methylene-bis-(6-(2H-benzotriazole-2-yl)-4-(1,1,3,3,-tetramethylbutyl)-phenol, and microparticulated ZnO.

18. A sunscreen composition according to claim 17 wherein the UV-A screening agent is 4-tert. butyl-4'-methoxydibenzoyl-methane.

19. A sunscreen composition according to claim 11 further comprising a UV-B screening agent.

20. A sunscreen composition according to claim 19 wherein the UV-B screening agent is octylmethoxycinnamate, a compound of formula II, or $TiO_2$.

21. A method of treating human skin or hair with a sunscreen composition comprising administering to the hair or skin of a human an effective amount of a composition of claim 1.

22. A method of treating human skin or hair with a sunscreen composition comprising administering to the hair or skin of a human an effective amount a composition of claim 4.

23. A method of treating human skin or hair with a sunscreen composition comprising administering to the hair or skin of a human an effective amount a composition of claim 11.

* * * * *

UNITED STATES PATENT AND TRADEMARK OFFICE
CERTIFICATE OF CORRECTION

PATENT NO. : 6,165,451
DATED : December 26, 2000
INVENTOR(S) : Alain Bringhen et al.

It is certified that error appears in the above-identified patent and that said Letters Patent is hereby corrected as shown below:

<u>Title page,</u>
Under Item [56] References Cited, a U.S. patent is missing. Therefore, please add -- 3,079,366 12/2000 Boyle et al. --;

<u>Column 14,</u>
Line 21, please change "gent" to -- agent --;

<u>Column 16,</u>
Line 11, after "amount" please add -- of --;
Line 16, after "amount" please add -- of --.

Signed and Sealed this

Fourth Day of December, 2001

Attest:

NICHOLAS P. GODICI
*Attesting Officer*     *Acting Director of the United States Patent and Trademark Office*